United States Patent [19]
Sterrett

[11] Patent Number: 5,378,146
[45] Date of Patent: Jan. 3, 1995

[54] POLYURETHANE BIOMEDICAL DEVICES & METHOD OF MAKING SAME

[75] Inventor: Terry L. Sterrett, Long Beach, Calif.

[73] Assignee: Ormco Corporation, Glendora, Calif.

[21] Appl. No.: 984,284

[22] Filed: Dec. 1, 1992

Related U.S. Application Data

[63] Continuation of Ser. No. 781,677, Oct. 24, 1991, abandoned, which is a continuation of Ser. No. 476,599, Feb. 7, 1990, abandoned.

[51] Int. Cl.$^6$ ............................................. A61C 3/00
[52] U.S. Cl. .................................... 433/11; 433/15; 433/18; 623/3; 623/11; 623/901
[58] Field of Search .................. 427/2, 38, 39; 623/3, 623/11, 901; 433/11, 15, 18, 23, 13

[56] References Cited

U.S. PATENT DOCUMENTS

| | | | |
|---|---|---|---|
| 4,490,229 | 12/1984 | Mirtich et al. | 204/192.15 |
| 4,613,517 | 9/1986 | Williams et al. | 427/2 |
| 4,656,083 | 4/1987 | Hoffman et al. | 428/265 |
| 4,718,905 | 1/1988 | Freeman | 427/2 |
| 4,764,394 | 8/1988 | Conrad | 427/39 |
| 4,772,325 | 9/1988 | Kwan et al. | 528/91 |
| 4,820,580 | 4/1989 | Hocker et al. | 428/304.4 |
| 4,919,659 | 4/1990 | Horbett et al. | 427/40 |
| 4,933,418 | 6/1990 | Sterrett | 433/11 |
| 4,944,947 | 7/1990 | Newman | 433/6 |
| 4,946,386 | 8/1990 | Kidd et al. | 433/11 |

OTHER PUBLICATIONS

Akovali et al, "Polymerization of Hexamethyl-disiloxane by Plasma on Activated Charcoal: Investigation of Parameters" Journal of Applied Polymer Science, vol. 29, 2617-2625, 1984.

Hoffman, Allan, "Biomedical Applications of Plasma Gas Discharge Processes: A Tutorial Presentation", Center for Bioengineering and Chemical Engineering, FL-20, University of Washington, Seattle, Wash pp. 699-703.

"Plasma Science PS1010 Continuous Plasma Surface Treatment" Plasma Science, Inc. 1987.

"PS0S00 Plasma Surface Treatment System", Plasma Science Inc, May. 1987.

"Plasma Pretreatment for Plastics" 1988 by Gardner Publications Inc. pp. 2-8.

"Plasma Polymerization of Hexamethydisiloxane", Robert A. Shepherd, Jr., Ph.D., Technical Notes, Plasma Science, Inc.

"Plasma Treatment", Peter W. Rose & Stephen L. Kaplan, Plasma Science Inc., Technical Notes, 1986.

"Gas Plasma Treatment of SPECTRA Fiber", S. L. Kaplan & P. W. Rose, Plasma Science Inc., Apr. 1988 No. 4.

"Ion Implanted Precipitate Microstructure & Mechanical Properties of Ceramic Surfaces" Metals/Materials Technology Series 1985.

"Effect of Silicon Ion Implantation on Mechanical Properties of Alumina" S. G. Pope & J. K. Cochran, 1988.

Ionic Atlanta, Inc. Brochure.

The Ionic Column, May 23, 1988.

Primary Examiner—George F. Lesmes
Assistant Examiner—Terrel Morris
Attorney, Agent, or Firm—Wood, Herron & Evans

[57] ABSTRACT

A polyurethane article and method of making same wherein the surface of the article had been subjected to a high energetic treatment wherein the surface characteristics has been modified.

6 Claims, 1 Drawing Sheet

POLYURETHANE BIOMEDICAL DEVICES & METHOD OF MAKING SAME

This application is a continuation of application Ser. No. 07/781,677, filed Oct. 14, 1991, now abandoned which is a continuation of application Ser. No. 07/476,599 filed Feb. 7, 1990 now abandoned.

The present invention is directed to biomedical and dental devices made of polyurethane which have been surface treated so as to provide improved biocompatibility and/or improved stain resistance.

BACKGROUND OF THE INVENTION

The interaction of polymeric materials such as urethane with the body has long been of interest to scientists, engineers, and clinicians. The success of a biomedical device depends upon its ability to withstand the physical and chemical environment to which they are subjected. Materials from which biomedical devices are made must exhibit sufficient biocompatibility to preclude rejection by the body or cause any harmful reaction such as inflammation or thrombus formation. The ability for a polymeric material to meet such criteria is dictated mainly by surface chemistry and to a lesser degree that of the bulk material.

Polyurethane elastomers are an example of a particular class of polymeric material that has found wide acceptance in biomedical applications. It has been established that the types of proteins adsorbed, and the nature of such adsorption, largely dictates the biocompatibility of the polyurethane material, assuming that other criteria related to biocompatability are met. Factors which affect the protein adsorption characteristics of polyurethane substrate include; processing, environment and urethane chemistry.

It has also been found that the method of fabrication of the material can alter its biocompatibility. For example, whether the material is cast or extruded can affect the blood contacting surface of the material and its thrombogenic properties. Extruded materials in certain instances are more thromboresistant than cast materials.

The thrombogenic properties of materials has commonly been related to the nature of proteins the surface absorbs. It has been demonstrated that certain classes of protein tend to decrease the thrombogenic properties of a material when adsorbed. For example, surfaces which preferentially adsorb albumin have been found to be relatively thromboresistant, while those surfaces which absorb fibrinogen tend to be highly thrombogenic. In the prior art, attempts have been made to alter the protein adsorption characteristics of the materials so as to decrease the thrombogenic properties. Various prior art surface treatments include; chemically grafting certain functional chemical groups to the polymer surface, hydrogel surfaces, attachment of pharmacologically active antithrombogenic surfaces and physical modifications. Such methods of surface treatment modifications have been used as a means of grafting or fixing a thin surface film. Such surfaces have typically been subjected to high energy treatment such as ion implantation or plasma deposition. These high energy treatments are used to treat the surface such that the surface becomes reactive and bonds with the film to be attached. The benefit of such films is that they are ultra-thin, are strongly bonded to the substrate and usually do not alter the mechanical properties of the base material. While such surface treatments as plasma or ion deposition have been used to affix a layer as described above, the prior art has not taught the use of these energetic treatments to alter the protein adsorption characteristics of the material.

It has also long been desirable in the orthodontic industry to improve the aesthetic properties of elastomeric orthodontic devices. Recently, it has become apparent that a great demand exists for orthodontic devices which have a minimal visual impact when viewed by others. As a result, a new generation of orthodontic brackets which are difficult to visually observe, have become much more available. Typically, such orthodontic brackets made out of ceramic or crystalline materials having a substantially clear appearance or a color substantially identical to the tooth. While such orthodontic devices have contributed significantly to improving the aesthetic appearance of orthodontic brackets, the elastomeric orthodontic tensioning devices used therewith, such as elastomeric O-rings and chains, detract or diminish the improvement such devices have provided due to staining and/or discoloration. Clinical experience has indicated that such ligatures and chains take on a discoloration or stained appearance within one to two weeks after application of the device. It is believed that the discoloration of these devices occur due to the same phenomenon that allows plaque formation. It is well known that the first step in plaque formation is the deposition of a protein layer to which larger macro molecules and/or other proteins adhere to. Their adhesion and subsequent denaturalization leads to a stained or discolored appearance typically associated with plaque. Therefore, it is desired to vary protein absorption to avoid this problem. With more aesthetic orthodontic brackets, discolored or stained ligatures become more noticeable, and thus detract from the overall appearance and benefits provided by the orthodontic bracket. While it is known that certain materials provide staining qualities, these materials lack the necessary strength to be used as orthodontic ligatures. Applicants have found that the stain resistant qualities of the orthodontic ligature made of an elastomeric urethane can be improved by reducing the protein adsorption of the ligature.

Applicants have invented an improved dental and biomedical devices wherein the protein adsorption characteristics thereof can be altered so as to provide improved biomedical compatibility or improved stain resistance without detracting from the strength of the material or product.

SUMMARY OF THE INVENTION

In one aspect of the invention there is provided an elastomeric polyurethane article of manufacture having an outer surface that has been subjected to a high energy surface treatment.

In another aspect of the present invention there is provided a method of making an elastomeric tensioning device comprising the steps of:
(a) providing a device made of a polyurethane elastomeric; and
(b) subjecting the surface of said device to a high energy treatment.

DETAILED DESCRIPTION OF THE INVENTION

Figure 1:
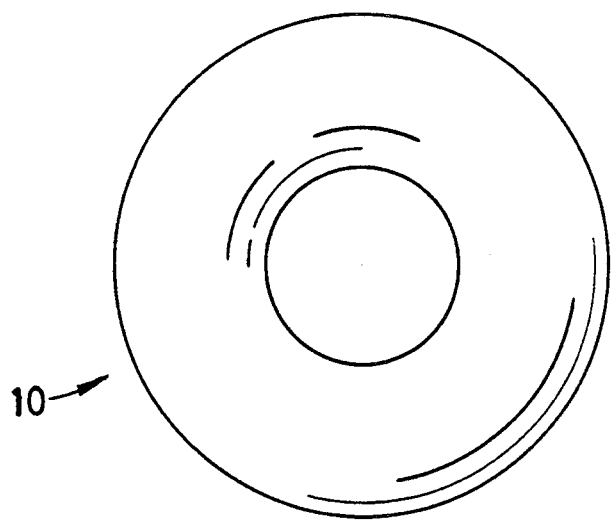
FIG. 1 is a front elevational view of an orthodontic elastomeric ligature used to fasten an orthodontic archwire to an orthodontic bracket.

Referring to FIG. 1 as illustrated an elastomeric orthodontic tensioning device 10 made in accordance with the present invention. In the particular embodiment illustrated, the orthodontic device 10 is an O-ring ligature used to secure an orthodontic bracket to an orthodontic arch wire. However, the elastomeric orthodontic tensioning device may comprise any other elastomeric device used in the mouth.

Figures 2, 3:
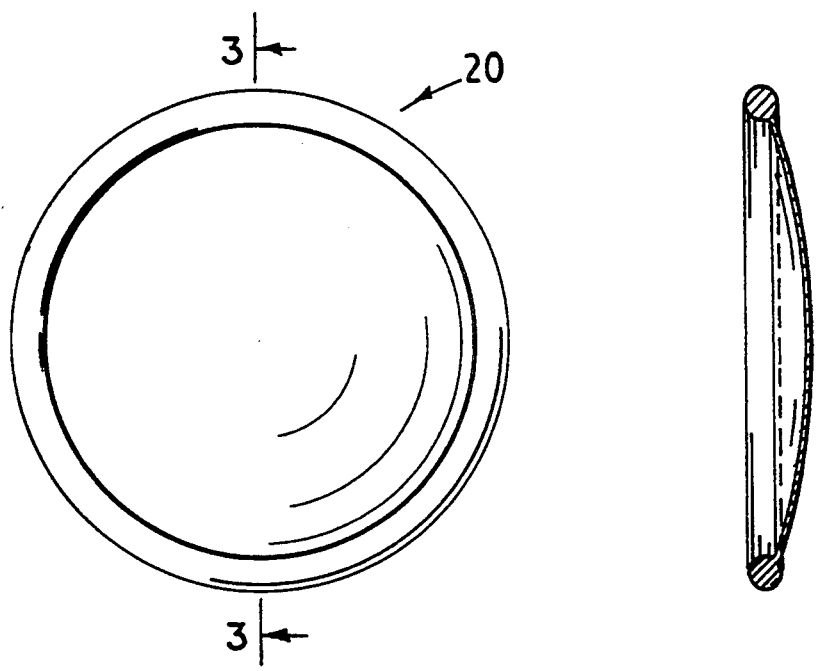
FIG. 2 is a front elevational view of a diaphragm for a blood pumping device made in accordance with the present invention.
FIG. 3 is a cross-sectional view of the device of FIG. 2 taken along line 3—3.

The elastomeric orthodontic device 10 is made of a polyurethane elastomer. In the particular embodiment illustrated, the device 10 is made of a thermoplastic polyurethane elastomer. While such materials provide sufficient structural strength, they are susceptible to staining. The outer surface 12 of the device 10 has been treated so as to improve its resistance to staining. In the embodiment illustrated, the surface 12 has been bombarded with ions. Preferably, positive ions are implanted on the surface of surface 12 of the device 10. FIG. 3 illustrates a schematic representation of a typical ion implantation method. The particular method of ion implantation is a well known and established procedure. An example of such procedure has been set forth by the Spire Corporation of Bedford, Mass. A detailed description of this method may be found in an article entitled "Tailoring Surface Properties by Ion Implantation" as published in the February, 1987 issue of *Materials Engineering* which is hereby incorporated by reference. In this process the device 10 is exposed to high energy ions that penetrate into shallow surface layers of the device. Typically, the depth of penetration is on the order of 100–200 angstroms. Preferably, the device 10 is made of a thermoplastic poly(ether) urethane elastomer and is bombarded with fluoride ions at 25 Kev at an ion concentration of about $1 \times 10^{14}$ ions/cm$^2$ for a time period of about 5 minutes. It is of course understood that the level of ion concentration and time period of exposure may vary in accordance with material being selected, and the desired surface modification. Ion implantation of test specimens did not adversely affect any of the mechanical properties of the urethane. Accordingly, the device 10 would maintain the necessary physical strength to act as an elastomeric ligature. Applicant has found that by providing a fluoride ion surface layer, the stain resistant qualities of the urethane may be significantly improved. Test specimens of a thermoplastic poly(ether)urethane (sold by Dow under the tradename PELLETHANE (2363-80) was subjected to an albumin protein adsorption test (which is described in detail later herein) after which the elastomer test specimens were rated for stain resistance. These results were compared with a test specimen of the same material which was not subjected to the fluoride ion treatment. The results are set forth in the following Table A.

TABLE A

| MATERIAL | SURFACE TREATMENT | 2 Hr. PROTEIN ADSORPTION (micro-g/cm$^2$) | STAIN* INDEX |
| --- | --- | --- | --- |
| Thermoplastic Poly(ether) | F$^+$, 25 Kev $1 \times 10^{14}$ ions/cm$^2$ | 30 | 3.0 |

TABLE A-continued

| MATERIAL | SURFACE TREATMENT | 2 Hr. PROTEIN ADSORPTION (micro-g/cm$^2$) | STAIN* INDEX |
| --- | --- | --- | --- |
| urethane Specimen | | | |
| Control Specimen (No Treatment) | — | 70 | 1.0 |

*Stain Index Rating:
0 = Completely Stained; Intense Yellow-Brown Discoloration
1 = Densely Stained; Intense Yellow-Brown Discoloration
2 = Stained; Yellow-Brown Discoloration
3 = Partially Stained; Yellow or Brown Discoloration
4 = Sparsely Stained; Slight Yellow or Brown Discoloration
5 = Original Appearance; No Discoloration The fluoride ion implantation provided significant improvement in stain resistance over the non-treated control sample. It is believed that the improved stain resistance resulted from the reduced protein adsorption characteristic of the treated specimen.

While the Applicant has found that fluoride ion implantation of the surface of the device provides significant improvement in stain resistance, the surface of the device 10 may be treated with other ions which will also significantly improve the stain resistant qualities. Test specimens of the same poly(ether)urethane previously discussed were subjected to an argon ion deposition of 25 Kev, $1 \times 10^{14}$ ions/cm$^2$ for a 5 minute time period. The mechanical properties of the specimens after argon ion bombardment remain substantially unchanged. The argon treated specimens were subjected to the same protein adsorption and stain resistant test conducted with the fluoride test specimen and compared to a non-treated (control) specimen. The results are set forth in Table B.

TABLE B

| MATERIAL | SURFACE TREATMENT | 2 Hr. PROTEIN ADSORPTION (micro-g/cm$^2$) | STAIN* INDEX |
| --- | --- | --- | --- |
| Thermoplastic Poly(ether) urethane Specimen | Ar$^+$, 25 Kev $1 \times 10^{14}$ ions/cm$^2$ | 46 | 2.0 |
| Control (No Treatment) | — | 72 | 1.0 |

*Same index as previously discussed with respect to fluoride in treatment.

Here again, stain resistance of the poly(ether)urethane with the argon ion treatment yielded significant improvement. Like the fluoride ion treated specimens, the protein adsorption was significantly reduced from the control.

Applicants have also found that other energetic surface treatments may be used to modify the protein adsorption characteristics of poly(ether)urethane so as to affect its biocompatibility and stain resistance. Both thermosetting and thermoplastic materials were tested under various plasma deposition chemistries. Test specimens were subjected to 300 watts of power for a time period of 5 minutes under various different plasma depositions. In the particular embodiment illustrated, the device was subjected to the following plasma chemistries: (1) $CF_4/CH_4$; (2) Ar; (3) $O_2$; (5) $CH_4$; (6) $C_2F_6/CH_4$. Table D provides a description of the process parameters for the various plasma deposition chemistries. The specimens tested were a thermoset poly(caprolactone)urethane sold by Acushnet Company under the tradename E 417-0, and thermoplastic poly(ethylene adipate)urethane sold by Mobay Plastic Division under the trademark TEXIN. The protein adsorption characteristics were measured and are set forth in Table C below.

TABLE C

| SAMPLE | SURFACE CHEMISTRY | PROTEIN ADSORPTION | |
|---|---|---|---|
| | | THERMOSET (micro-g/cm$^2$) | THERMOPLASTIC (micro-g/cm$^2$) |
| Control | — | 4.9 | 26.0 |
| 4 | O2 | 10.8 | 57.8 |
| 3 | O2/CF4 | 11.5 | 24.2 |
| 2 | Ar | 8.6 | 17.6 |
| 1 | CF4/CH4 | 5.1 | 15.3 |
| 5 | CF4 | 4.3 | 12.5 |
| 6 | CH4 | 4.6 | 9.2 |
| 7 | C2F6/CH4 | 3.5 | 6.7 |

The protein adsorption of each sample was determined using albumin (bovine) fraction IV, Sigma Chemical and 125I-albumin, Radio Chemicals. A stock protein solution containing 237 microgram/ml albumin and phosphate buffered saline (PBS, pH 7.4) was prepared and was spiked with 10 microliter of 125I-albumin, specific activity 0.757 μCi/ml. Samples of materials exposed to the plasma deposition were submersed in a solution, thus denoting time zero. After the desired submersion time, samples were moved from the test solution and rinsed with distilled water for 30 seconds. For the present instance a 2 hour submersion time period was used. The samples were placed in a vial and radioactivity was assayed using a sodium iodide, thallium-activated solid scintillation detector.

The plasma depositions as outlined by Table D were applied using a PS 0500 plasma treatment system available from Plasma Science Inc. of Belmont, Cal. Each chemistry was applied at 300 watts of power for a period of 5 minutes. The control sample was not subjected to any of the depositions. As can be seen from Table C, the various plasma treatment depositions either increased or decreased the protein adsorption of albumin. The specimen treated with O2 significantly improved the albumin adsorption, and thus, provides improved biomedical compatibility. The various other plasma surface treatments decreased the albumin adsorption, thus providing improved stain resistance characteristics which are not the same.

treatments were observed. The resulting change in contact angles did not, however, yield the same magnitude of reduction in the protein adsorption as that found in the thermoset poly(ethylene adipate)urethane. In general, protein adsorption was reduced by no more than 30% for polycaprolactone. Surface treatments which decrease contact angle resulted in increased protein adsorption for both substrates investigated. With regard to polycaprolactone, it was found that protein adsorption increased 116% when the contact angle was decreased 54%. By comparison, a 40% decrease in contact angle for the thermoplastic poly(ethylene adipate)urethane using the same plasma chemistry, resulted in a 48% increase in albumin protein adsorption. Thus, it can be seen by appropriately providing the appropriate energetic surface treatment, i.e., ion deposition or plasma deposition with the appropriate chemistry the surface characteristics of the urethane may be modified, without changing the physical characteristics of the materials, so as to obtain the appropriate desired physical characteristics. For example, depending on the base urethane material, the surface may be treated with an appropriate plasma or ion deposition so as to improve its biomedical compatibility, by improving the albumin adsorption, or improved stain resistance and by decreasing its protein adsorption.

FIG. 2 illustrates a biomedial implant device 20 which has been subjected to plasma deposition in order to improve its biocompatibility. In the particular embodiment illustrated, device 20 is a diaphragm for a blood pumping device made of an appropriate polyurethane. However, it is to be understood that any other elastomeric polyurethane may be employed as desired.

Upon exposure to blood synethetic materials are quickly coated with plasma protiens. Many researchers have reported that if the protein coating is primarily fibrinogen platelet adhesion greatly increases. Alternatively materials which primarily adsorbed albumin do not readily adhere platelets. In effect albuminated surfaces tend to be passivated, thus exhibiting low platelet adhesion. The importance of platelet adhesion to blood contacting biomaterials is that thrombus formation is initatiated by such adhesion therefore, it is the desirable to minimumize the thrombogenic properties of the blood contacting materials through techniques such as surface passivation via coating by albumin.

TABLE D

| CHEMISTRY | CLASSIFICATION OF PLASMA TREATMENT | GAS MIXTURE % | STARTING TEMP (Co) | FINAL TEMP (Co) | PRESSURE (Torr) |
|---|---|---|---|---|---|
| 1. O2 | Oxidation | 100 | 29 | 44 | 0.163 |
| 2. CF4 | Fluorine Substitution | 100 | 30 | 44 | 0.180 |
| 3. CH4 | Hydrocarbon Surface Crosslinking | 100 | 30 | 30 | 0.127 |
| 4. C2F6/CH4 | Fluorine Deposition Followed By Plasma Polymerization | 77/23 | 33 | 47 | 0.175 |
| 5. O2/CF4 | Oxidation | 50/50 | 29 | 44 | 0.160 |
| 6. Ar | Surface Crosslinking And/Or Surface Ablation | 100 | 30 | 38 | 0.315 |
| 7. CF4/CH4 | Fluorine Deposition Followed By Plasma Polymerization | 77/23 | 30 | 30 | 0.135 |

In general, it was found that when the contact angle of the substrates was increased by plasma deposition, the level of albumin adsorbed onto the substrate decreased. This effect was observed to be the greatest substrate with the polyurethane adipate substrate. An increase in contact angle of 30–71% yielded a decrease in 2 hours protein adsorption of 52–74% for poly(ethylene)adipate. Comparable changes in contact angles for polycaprolactone as a result of the same plasma In contrast it has been found that when erythrocyte adhesion and spreading are considered, albuminated surfaces tend to activate adhesion. Whereas those coated with fibrinogen minimumize adhesion and spreading. Therefore with respect to erythrocyte adhesion and spreading, fibrinogen acts as a passivating agent and albumin tends to activate.

The present invention provides for a method in which to increase or decrease albium adspertion as needed.

In summary, Applicants have developed an improved polyurethane surface treatment which provides the capability of surface treating the polyurethane to provide appropriate biocompatibility and/or stain resistance. It is to be understood that while the present invention has set forth specific urethane and energetic chemistries, various modifications and changes may be made without departing from the scope of the present invention. The present invention being limited by the following claims.

What is claimed is:

1. An orthodontic tensioning device which is subject to substantial elongation during use, said device made of an elastomeric thermoplastic polyurethane material, the outer surface of said orthodontic tensioning device having been subjected to ion implantation such that said device possesses properties of reduced protein adsorption and improved stain resistance, wherein said implanted ions are selected from the group consisting of fluoride and argon, and wherein said device retains its reduced protein adsorption and improved stain resistance properties during elongation.

2. The orthodontic tensioning device of claim 1 wherein said ion implantation was provided at 25 Kev at an ion concentration of $1 \times 10^{14}$ ion/cm$^2$.

3. An orthodontic tensioning device which is subject to substantial elongation during use, said device made of an elastomeric thermoplastic polyurethane material, the outer surface of said orthodontic tensioning device having been subjected to plasma deposition such that said device possesses properties of reduced protein adsorption and improved stain resistance, wherein said deposited plasma is selected from the group consisting of $O_2/CF_4$, Ar, $CF_4/CH_4$, $CF_4$, $CH_4$ and $C_2F_6/CH_4$, and wherein said device retains its reduced protein adsorption and improved stain resistance properties during elongation.

4. The orthodontic tensioning device of claim 3 wherein said plasma deposition is provided at 25 Kev and at 300 watts of power.

5. An orthodontic tensioning device which is subject to substantial elongation during use, said device made of an elastomeric thermosetting polyurethane material, the outer surface of said orthodontic tensioning device having been subjected to plasma deposition such that said device possesses properties of reduced protein adsorption and improved stain resistance, wherein said deposited plasma is selected from the group consisting of $CF_4$, $CH_4$ and $C_2F_6/CH_4$, and wherein said device retains its reduced protein adsorption and improved stain resistance properties during elongation.

6. The orthodontic tensioning device of claim 5 wherein said plasma deposition is provided at 25 Kev and at 300 watts of power.

* * * * *